(12) United States Patent
Madaus et al.

(10) Patent No.: US 6,530,372 B1
(45) Date of Patent: Mar. 11, 2003

(54) AUTOMATIC RESPIRATION UNDER POSITIVE AIRWAY PRESSURE

(75) Inventors: Stefan Madaus, Krailling (DE); Harald Vögele, München (DE); Jutta Griebel, Pflaumdorf (DE)

(73) Assignee: MAP Medizintechnik für Arzt und Patient GmbH (DE)

(*) Notice: Subject to any disclaimer, the term of this patent is extended or adjusted under 35 U.S.C. 154(b) by 0 days.

(21) Appl. No.: 09/403,518
(22) PCT Filed: Apr. 22, 1998
(86) PCT No.: PCT/EP98/02381
§ 371 (c)(1),
(2), (4) Date: Dec. 6, 1999
(87) PCT Pub. No.: WO98/47554
PCT Pub. Date: Oct. 29, 1998

(30) Foreign Application Priority Data
Apr. 23, 1997 (DE) .......................... 197 17 106

(51) Int. Cl.⁷ .......................... A61M 16/00; A62B 7/00; F16K 31/02
(52) U.S. Cl. .............................. 128/204.23; 128/204.18
(58) Field of Search ..................... 128/204.18, 204.21, 128/204.23, 204.26

(56) References Cited

U.S. PATENT DOCUMENTS

| | | | |
|---|---|---|---|
| 5,134,995 A | * 8/1992 | Gruenke et al. | 128/204.23 |
| 5,239,995 A | * 8/1993 | Estes et al. | 128/204.23 |
| 5,259,373 A | * 11/1993 | Gruenke et al. | 128/204.23 |
| 5,492,113 A | * 2/1996 | Estes et al. | 128/204.23 |
| 5,549,106 A | * 8/1996 | Gruenke et al. | 128/204.23 |
| 5,551,418 A | * 9/1996 | Estes et al. | 128/204.23 |
| 5,551,419 A | * 9/1996 | Froehlich et al. | 128/204.23 |
| 5,704,345 A | * 1/1998 | Berthon-Jones | 128/204.23 |
| 5,794,614 A | * 8/1998 | Guenke et al. | 128/204.21 |
| 6,457,472 B1 | * 10/2002 | Schwartz et al. | 128/204.23 |

FOREIGN PATENT DOCUMENTS

| | | | |
|---|---|---|---|
| EP | 651971 A1 | 5/1995 | A61B/5/113 |
| EP | 722747 A2 | 7/1996 | A61M/16/00 |
| WO | WO 92/11054 | 7/1992 | A61M/16/00 |
| WO | WO 93/08857 | 5/1993 | A61M/16/00 |

OTHER PUBLICATIONS

Chest, vol. 110, pp. 1077–1088, Oct. 1996, "The Pharyngeal Critical Pressure: The Whys and Hows of Using Nasal Continuous Positive Airway Pressure Diagnostically".
Sleep, vol. 19, No. 10, pp. 184–188, 1996, "Structural Basis for Alterations in Upper Airway Collapsibility".

* cited by examiner

Primary Examiner—Aaron J. Lewis
Assistant Examiner—Joseph F. Weiss, Jr.
(74) Attorney, Agent, or Firm—Ohlandt, Greeley, Ruggiero & Perle, LLP; George W. Rauchfuss, Jr.

(57) ABSTRACT

The present invention provides an automated respiration method involving positive airway pressure. The method comprises a step for measuring the respiratory gas flow and comparing it with a threshold value. A further step is provided for assessing any obstructive respiratory disturbance. An evaluation step evaluates the measurement values and determines whether it is a case of normal breathing, obstructive respiratory disturbance, non-obstructive respiratory disturbance or snoring. Depending on the results provided by the evaluation step, the positive airway pressure is either maintained or modified. It is the advantage of the invention that the respiratory gas flow as well as the airway obstruction are continuously measured, thereby enabling the positive air pressure to be adjusted to different individual states of the patient.

15 Claims, 5 Drawing Sheets

AUTOMATIC RESPIRATION UNDER POSITIVE AIRWAY PRESSURE

Figure 1:
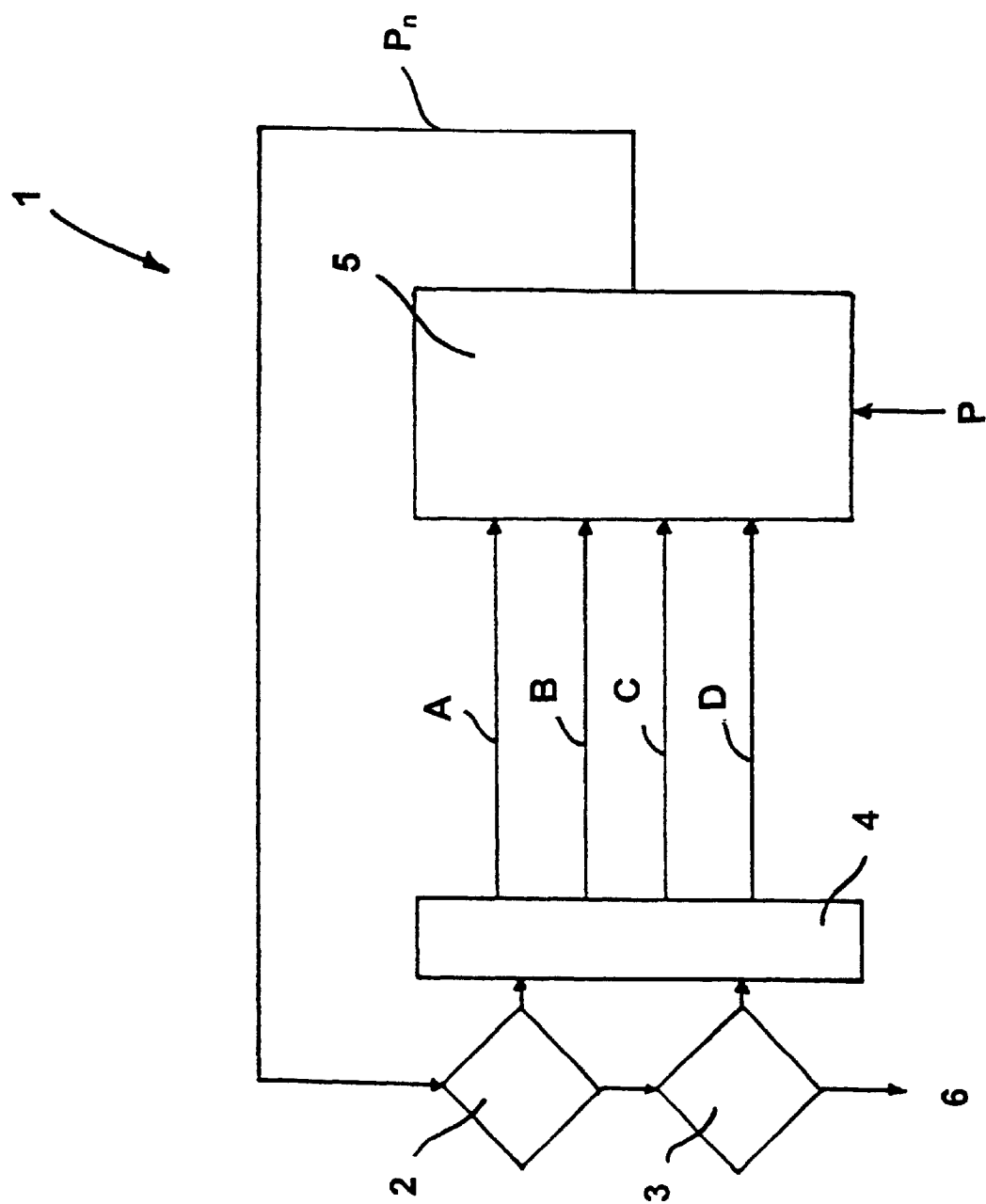

The invention relates to an apparatus for automated respiration, for example in the CPAP (continuous positive airway pressure) therapy and in the biPAP (biphase positive airway pressure) therapy. In the CPAP therapy, a positive air pressure is continuously exerted onto the airways; wherein a pneumatic fixation of the upper airways is achieved and an obstructive respiratory disturbance (sleep apnea respiratory standstill during sleeping) should be avoided. In the biPAP therapy the pressure is exerted intermittently. In both cases, the pressure level is individually adjusted to the patient.

In positive pressure respiration the positive airway pressure is used either continuously (continuous positive airway pressure: CPAP) or intermittently (biphase positive airway pressure: biPAP) via a nose mask or nose-mouth mask. This type of therapy is based on the concept that due to a pressure of 5 to 25 mbar the airways in the pharynx can be kept open and that the patient can thus inhale and exhale without hindrance. However, since the CPAP or biPAP apparatuses existing so far do not measure the respiratory gas flow, there is the risk that an applied respiration pressure is not linked with a normal respiratory flow. Since the respiratory flow is not measured directly, complicated diagnostic methods have to be used to document the effectiveness of the respiration therapy (polysomnographic diagnosis and adjusting the respiration therapy over several nights in a sleep laboratory). At present, no CPAP/biCPAP apparatus is known which measures simultaneously quantitatively the respiratory gas flow and the obstruction of the airways.

It is known that there is a critical pressure for a collapse of the upper airways. For example, from CHEST, Vol. 110, pages 1077–1088, October 1996, and Sleep, Vol. 19, No. 10, pages 184–188 it is moreover known to avoid sleep apnea by means of a CPAP therapy in which a positive air pressure above the critical pressure is continuously supplied to the patient during sleep. In this case it is assumed that the critical pressure is assessed for each patient prior to the therapy. Moreover, it is intended to measure the critical pressure after the treatment in order to evaluate the success of the therapy. Moreover, it is known from the prior art to determine the critical air pressure as an intersecting point between a straight line through measuring values of the maximum respiratory gas flow at different positive air pressures, said values being inserted into a diagram above the positive air pressure, and the axis of this pressure.

[1] Translator's note: Error in the original German text: should read "No. 10"

The required effective CPAP pressure, e.g. in a CPAP respiration apparatus, is not a constant value but varies in accordance with the body position, the sleeping phase and changes in the body weight or if alcohol is consumed or medicines are taken. The effective respiration pressure thus depends on different factors. CPAP apparatuses known so far are not able to modify the effective respiration pressure in accordance with these factors. For example, it is known that most patients need a higher effective respiration pressure when lying on their backs than when being in a lateral position. The reason therefor resides in that the critical collapse pressure and the airway resistance change in accordance with the above factors. The known CPAP apparatuses cannot measure the airway resistance and the collapsibility. In order to nevertheless guarantee an effective respiration during the entire period of sleep, the effective respiration pressure is as a rule adjusted at a higher value than would be necessary. Thus, the effective pressure is adjusted such that there is no respiratory disturbance if the patient lies on the back. However, if the patient always sleeps in a lateral position, this means that during the entire night the patient is supplied with a too high respiration pressure.

Thus, it is a disadvantage of the prior art that individual breathing changes of a patient caused, for example, by occurring snoring, body position changes, sleep phase changes, consumption of alcohol or health disturbances during the therapy cannot be taken into consideration.

In contrast thereto, it is the problem of the invention to provide an improved apparatus for automated respiration.

In solving this problem, the invention is based on the principal idea of continuously measuring the respiratory gas flow in the apparatus during respiration and examining for an obstructive airway disturbance.

Thus, the invention can essentially serve two purposes: On the one hand, an automation of the CPAP or biPAP adjustment and, on the other hand, an automatic adjustment of the effective CPAP or biPAP pressure to individual changes of the mechanics of breathing, for example caused by changes in the body position during sleep.

When initiating a nasal respiration therapy, the initially adjusted respiration pressure is modified by the invention in accordance with the measured respiratory gas flow. The initial respiration pressure ($P_n$=k) is given by the doctor. The threshold value for normal respiratory gas flow is also given by the doctor. Both values are inputted into the apparatus. On the basis of both values ($P_n$ and respiratory gas flow threshold value) the invention can automatically change the nasal respiration pressure to such an extent that the patient does no longer have any respiration disturbances and has a normal respiratory flow.

It is the advantage of the invention that the respiratory gas flow and the airway obstruction ($P_{crit}$, airway resistance, flow limitation) are measured continuously, and the positive air pressure is modified accordingly. It is thus possible to treat the patient with a lower respiration pressure, e.g. during respiration at home. It is a further advantage of the present invention that, for example during respiration at home, an effective respiration pressure with normal respiratory flow is guaranteed at any time.

Figure 2:
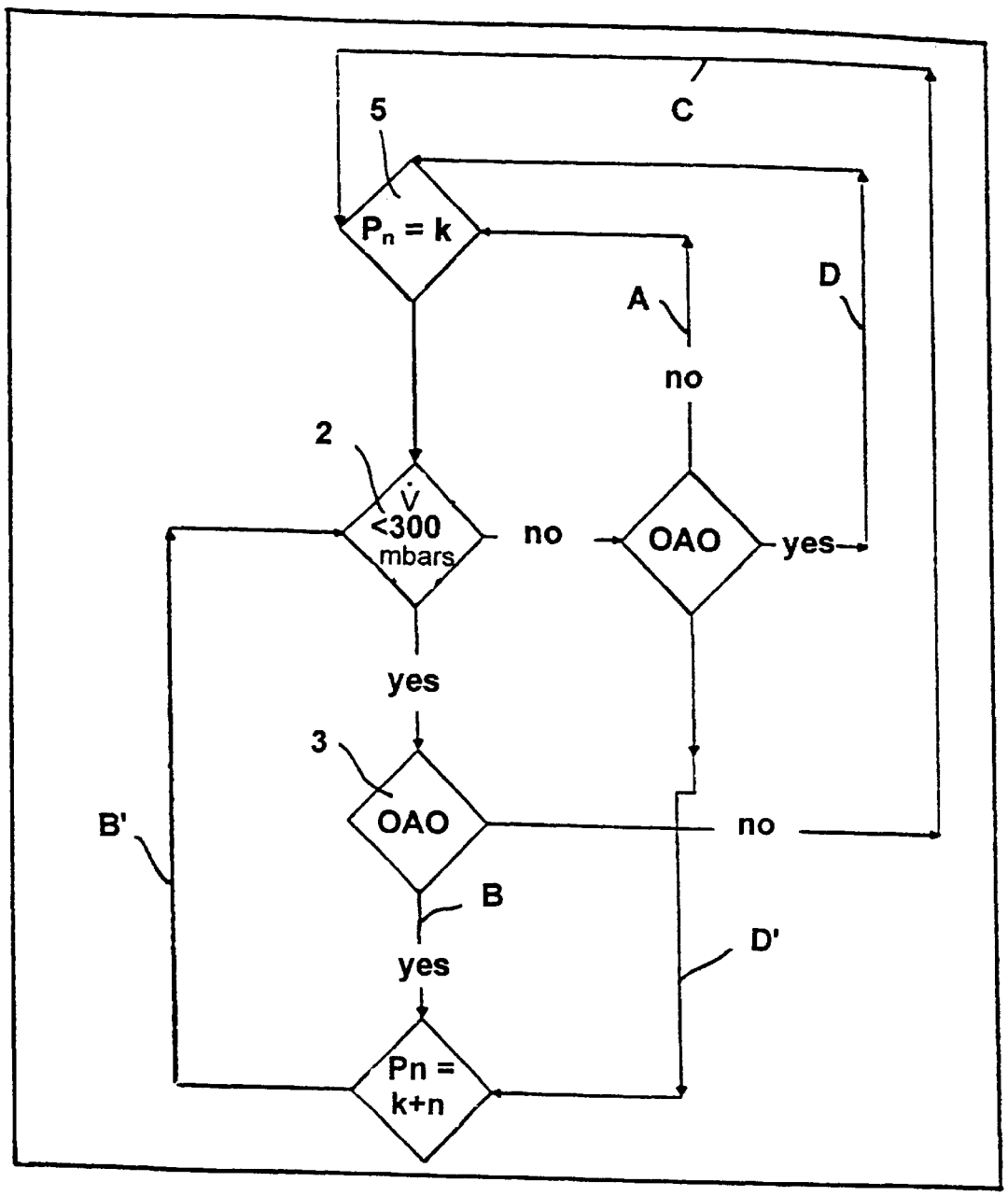
Figure 3:
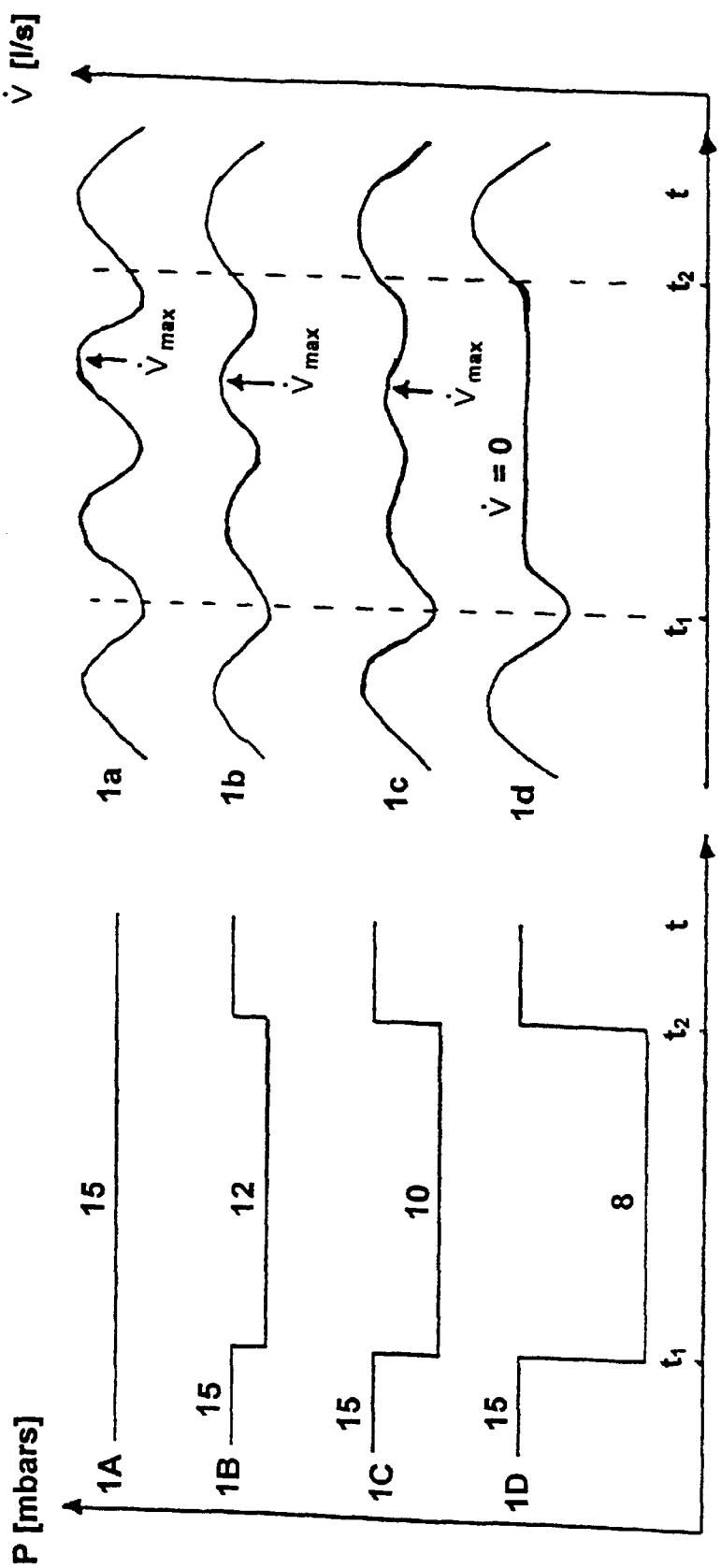
Figure 4:
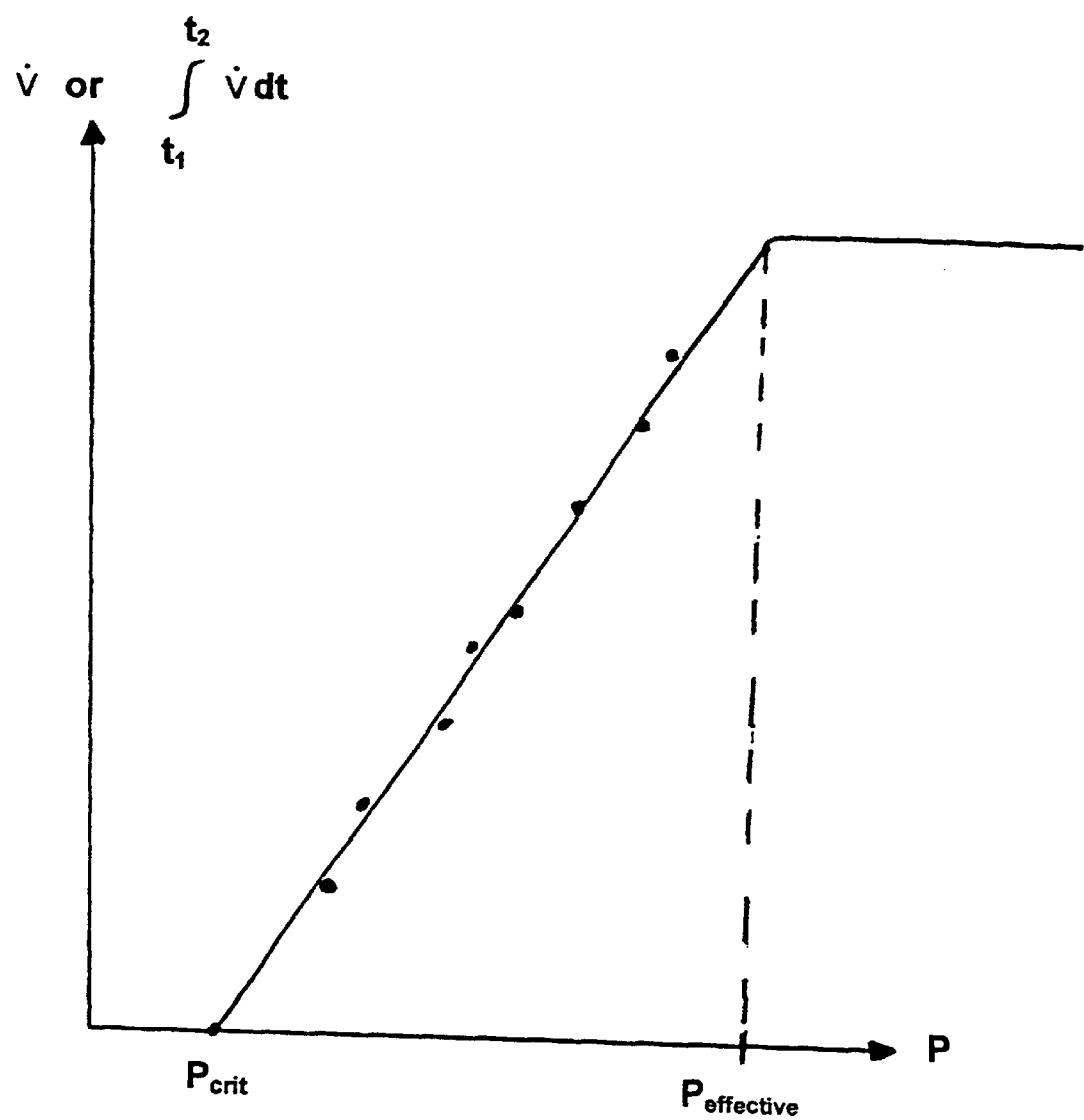
Figure 5:
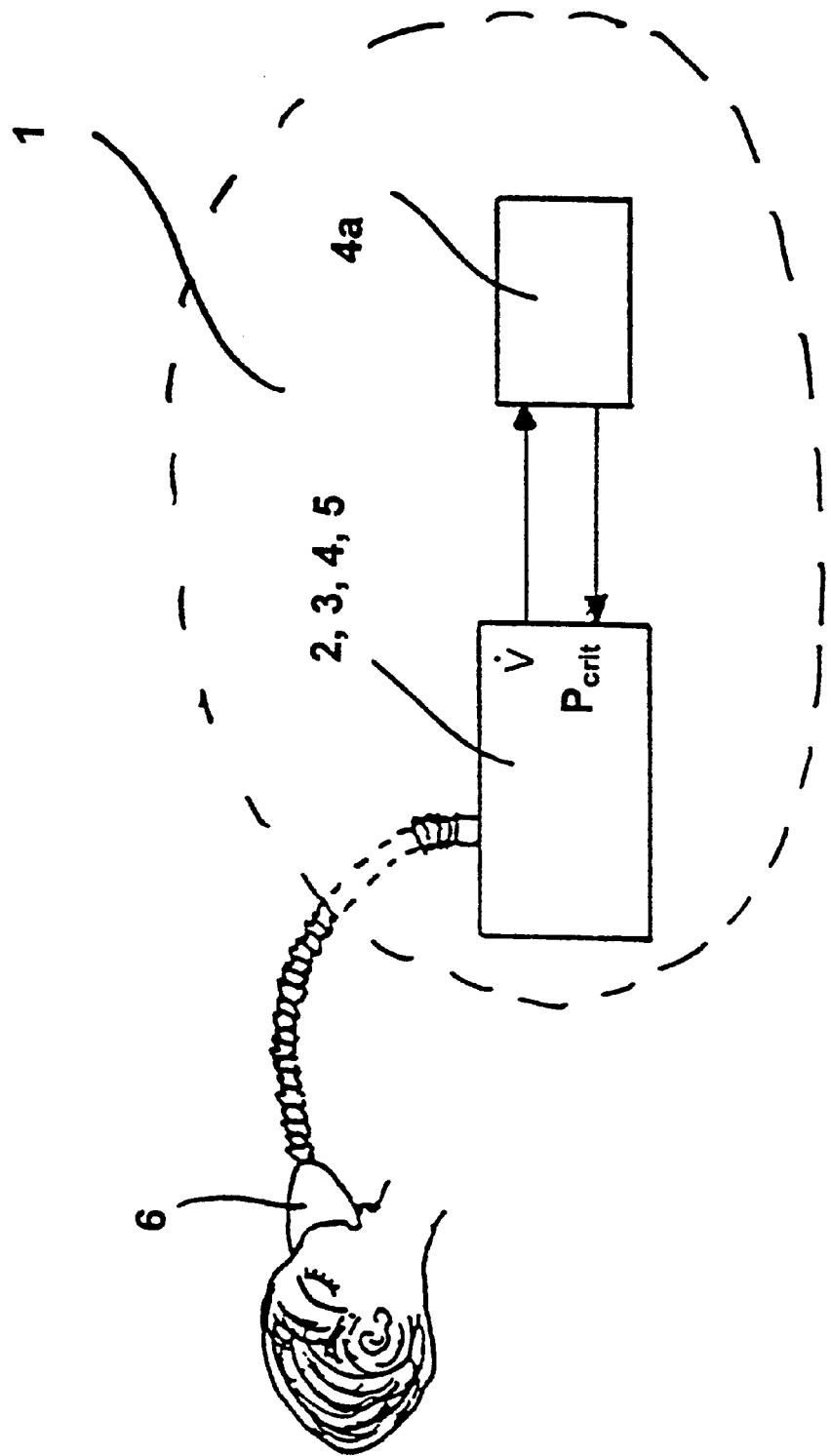

In the following the invention is described in more detail in connection with the drawings in which FIG. 1 shows a block diagram of the apparatus of the present invention, FIG. 2 shows an algorithm for the automatic adjustment of the effective positive air pressure, FIG. 3 shows a diagram illustrating the method of collapsibility measurements of the respiratory gas flow in accordance with the decrease of the positive air pressure (measurements of the respiratory flow in accordance with the decrease of the positive air pressure), FIG. 4 shows a diagram for determining the critical collapse pressure Pcrit from the maximum values of the respiratory gas flow curve or the integrals of the respiratory gas flow at different positive air pressures, and FIG. 5 shows the apparatus of the present invention used by a patient.

FIG. 1 shows a block diagram of the apparatus of the present invention. The apparatus 1 comprises a pressure adjusting means 5 adjusting a respiration pressure P to a pressure $P_n$ so that a positive air pressure is continuously exerted onto the upper airways of a patient via a respiration mask 6. A means 2 is provided for measuring the respiratory gas flow of a patient. Moreover, the apparatus 1 comprises a means 3 for assessing an obstructive respiratory disturbance. The measuring results of the means 2 and 3 are supplied to an evaluation means 4 which determines whether it is a case of normal breathing A, obstructive respiratory disturbance B, non-obstructive respiratory disturbance C or snoring D. The diagnosis results A through D are supplied to the pressure adjusting means 5 as a signal.

FIG. 2 shows an algorithm for adjusting or adapting the positive air pressure. The doctor adjusts an initial respiration pressure $P_n=k$ and the threshold value for the respiratory flow $V_{min}$. In accordance with the invention, the initial pressure $P_n=k$ ($k=\pm 1,2,3$) can be changed automatically in accordance with the measured respiratory gas flows. As becomes clear from this Figure, the combination of measuring the respiratory gas flow and the upper airway obstruction (OAO) allows the assessment of normal breathing (A) or the assessment of obstructive sleep-related respiratory disturbances (B) or the assessment of non-obstructive respiratory disturbances. If in case B the obstructive respiratory disturbance is not eliminated after increasing the air pressure to k+n, the connection B' allows for a feedback to means 2 for assessing whether there is a technical fault. Snoring (D), which can be linked with normal respiratory flows, is a special case. Since snoring is considered to be a risk factor for cardiovascular diseases, many doctors recommend to eliminate also snoring alone by increasing the CPAP pressure. This is solved by the connection D'. D' is initiated if snoring is monitored over a relatively long period of time; then, the nasal respiration pressure can be increased until the airway obstruction no longer occurs. Thus, the invention can distinguish between obstructive and non-obstructive respiratory disturbances. In the case of obstructive respiratory disturbances, the respiration pressure can be modified automatically by measuring the respiratory gas flow and the airway obstruction such that a normal respiratory gas flow without airway obstruction is generated. In the case of respiratory disturbances without obstruction of the upper airways (D), the respiration apparatus can shift into a different therapy mode, e.g. biPAP therapy. A biPAP therapy is necessary if the obstructive sleep apnea is linked with simultaneous central respiratory disturbances. Central respiratory disturbances with obstructive sleep apnea occur preferably only occasionally, e.g. only during REM sleep or only in specific body positions. Moreover, central respiratory disturbances with obstructive sleep apnea occur only if diseases of the respiratory muscles (respiratory pump) exist, such as, for example, in the case of restrictive and obstructive lung diseases or if disturbances of the respiratory drive exist, for example during REM sleep, in the case of adiposity, neuromuscular diseases or cardiac diseases. Since in the case of these diseases a CPAP therapy alone is not sufficient, a biPAP therapy must be applied. It is the advantage of the invention that it is possible to automatically switch from the CPAP mode to the biPAP mode, and the patient can thus be supplied with sufficient air in accordance with the ventilation of the lung (tidal volume and respiratory gas flow). The CPAP/biPAP apparatuses known so far cannot switch automatically.

By means of the invention, the respiration pressures can automatically be adapted to the different conditions leading to sleep-related respiratory disturbances. Thus, firstly the safety of respiration at home can be improved, secondly all respiration pressures can be adjusted at a lower level than in the existing therapy, and thirdly side effects of the existing respiration therapy can be reduced.

The measurement of the upper airway obstruction in means 3 is performed according to the principle of measuring the collapsibility of the upper airways. The collapsibility and the critical collapse pressure are measured according to the principle as published in CHEST Vol. 110, pages 1077 to 1088, October 1996. It is the principle of measuring the collapsibility that the nasal respiration pressure is decreased in a very special algorithm without thereby disturbing the sleep. At the same time, the respiratory flow is measured at different pressure steps and entered into a flow pressure diagram. By determining the regression straight line of the flow pressure diagram, the airway resistance of the upper airways can be measured and the so-called critical collapse pressure ($P_{crit}$) can be determined. The principles of measurement and evaluation can be taken from FIGS. 3 to 5.

FIG. 3 shows the influence of different positive air pressures onto the respiratory gas flow $\dot{V}$ to and from the patient. FIG. 3 shows a normal, unhindered respiratory gas flow 1a at a positive air pressure of 15 millibars (1A). If the air pressure is decreased to 12 millibars (1B) during the period from $t_1$ to $t_2$ (e.g. during about 3 breaths), there is a reduced amplitude of the respiratory gas flow 1b during this time interval. A further decrease of the pressure to 10 millibars (1C) further reduces the respiratory amplitude to the respiratory gas flow 1c. After reducing the positive air pressure to 8 millibars (1D), the critical air pressure is reached. This is shown in curve 1d by the standstill of the respiratory gas flow during the period of $t_1$ to $t_2$, wherein $\dot{V}$ becomes zero. In the curves 1a through 1c, $\dot{V}_{max}$ (arrows) is different from zero. In FIG. 3 the pressure reduction intervals $t_1 \ldots t_2$ in the sequence 1A ... 1D are shown one above the other. In fact, these reductions take place one after the other during e.g. one period comprising a total of 20 breaths for a reduction cycle with 4 different pressure values. This cycle is repeated, for example, each 5 to 10 minutes.

Translator's note: Error in the original German text: should correctly read "FIG. 3"

FIG. 4 shows a diagram by means of which the critical pressure $P_{crit}$ can be determined. A straight line is drawn through measuring values of respiratory gas flow curves in a program for determining the critical pressure $P_{crit}$ according to FIG. 3, said straight line having the smallest possible distance from the measuring values and compensating the natural dispersion of the measuring values. The measuring points are determined during the therapy from the respiratory gas flow curves in which $\dot{V}_{max}$ is different from zero. By extrapolation of the straight line, the critical collapse pressure and the airway resistance of the patient can thus be assessed automatically during sleep.

Alternatively, also the integrals of the respiratory gas flow can be determined during the period from $t_1$ to $t_2$ and entered into the diagram as measuring points. The intersecting point between the abscissa and a straight line drawn through said points also leads to the critical pressure $P_{crit}$.

According to FIG. 5, the respiratory gas flow signal $\dot{V}$ generated in means 2 via respiration mask 6 is passed to a computer 4a which calculates the critical pressure $P_{crit}$ and the airway resistance and controls the desired value of the positive air pressure $P_n$ in means 5 such that it is either maintained or changed accordingly. The measurement of the respiratory gas flow with pressure reduction takes place in time intervals being individually adjusted to the patient.

The effective CPAP pressure $P_{effective}$ is the pressure during which normal respiratory gas flow prevails and an increase in the pressure does not lead to an increase in the respiratory gas flow.

An obstructive respiratory disease can also be assessed by determining the respiratory flow resistance or the respiratory flow limitation.

What is claimed is:

1. A method for automated respiration of a patient involving positive airway pressure, comprising the steps of:
   (a) supplying a patient with air at a positive air pressure,
   (b) providing a preset, normal positive airway pressure (Pn) for the supplying of air to the patient,
   (c) measuring the respiratory gas flow (V) of the patient,
   (d) assessing a critical collapse pressure (Pcrit), and a respiratory flow resistance or a respiratory flow limitation, wherein said critical collapse pressure (Pcrit) is determined by measuring the respiratory gas flow ($\dot{V}$) at a positive air pressure (P) guaranteeing that the airways are completely open, gradually decreasing (1B, 1C, 1D) the positive air pressure (P) and measuring the respective respiratory gas flow ($\dot{V}$) in a time interval ($t_1 \ldots t_2$), wherein $\dot{V}$ does not become zero, and integrating the respective respiratory gas flow ($\dot{V}$) over the time interval ($t_1 \ldots t_2$), calculating a straight line having the smallest possible distance from the values of the integrals as a function of the positive air pressure (P), and determining the critical air pressure (Pcrit) from the straight line at the integral value zero,
   (e) assessing on the basis of the measurement results of steps (c) and (d) whether the patient is experiencing a case of normal breathing (A), obstructive respiratory disturbance (B), non-obstructive respiratory disturbance (C) or snoring (D), and
   (f) maintaining or modifying the normal positive airway pressure (Pn) in accordance with the assessments of said step (e).

2. The method according to claim 1, wherein it is assessed that
   (a) it is a case of normal breathing (A) if a maximum respiratory gas flow ($\dot{V}$max) is measured being larger than or equal to a threshold value for respiratory gas flow ($\dot{V}$) and any values of an obstructive respiratory disturbance (B) are not assessed,
   (b) it is a case of obstructive respiratory disturbance (B) if a maximum respiratory gas flow ($\dot{V}$max) is measured as being smaller than the threshold value for respiratory gas flow ($\dot{V}$) and an obstructive respiratory disturbance (B) is assessed,
   (c) it is a case of non-obstructive disturbance (C) if a maximum respiratory gas flow ($\dot{V}$max) is measured as being smaller than the threshold value for respiratory gas flow ($\dot{V}$) and any values of an obstructive respiratory disturbance (B) are not assessed, and
   (d) it is a case of snoring (D) if a maximum respiratory gas flow ($\dot{V}$max) is measured as being larger than or equal to the threshold value for respiratory gas flow ($\dot{V}$) and the values of an obstructive respiratory disturbance are assessed.

3. The method according to claim 2, wherein,
   (a) the preset, normal positive air pressure (Pn) is maintained if it is a case of normal breathing (A),
   (b) the positive air pressure is increased if it is a case of obstructive respiratory disturbance (B),
   (c) a different therapy mode is switched to if it is a case of non-obstructive respiratory disturbance (C), and
   (d) the positive air pressure is increased if it is a case of snoring (D), wherein the pressure increase is terminated if, upon increase of the positive air pressure, the maximum respiratory gas flow ($\dot{V}$ max) is not further increased.

4. The method according to claim 3, wherein in case (c) the switch is from monolevel to bilevel CPAP therapy.

5. The method according to claim 2, wherein the threshold value of the respiratory gas flow ($\dot{V}$) is adjusted in accordance with physiological values of a patient.

6. The method according to claim 5, wherein the respiratory gas flow ($\dot{V}$) is measured in intervals of time which are individually adjusted to a patient.

7. The method according to claim 6, wherein the adjustment of the threshold value of the respiratory gas flow ($\dot{V}$) in accordance with physiological values of the patient is 300 ml/s.

8. A method for automated respiration of a patient involving positive airway pressure, comprising the steps of:
   (a) supplying a patient with air at a positive air pressure,
   (b) providing a preset, normal positive airway pressure (Pn) for the supplying of air to the patient,
   (c) measuring the respiratory gas flow ($\dot{V}$) of the patient,
   (d) assessing a critical collapse pressure (Pcrit), and a respiratory flow resistance or a respiratory flow limitation, wherein said critical collapse pressure (Pcrit) is determined by
      measuring the maximum respiratory gas flow ($\dot{V}$ max) at a positive air pressure (Pn) guaranteeing that the airways are completely open,
      gradually decreasing (1B, 1C, 1D) the positive air pressure ($P_n$) and measuring the respective respiratory gas flow ($\dot{V}$), and
      calculating a straight line having the smallest possible distance from the measuring values of the maximum respiratory gas flow ($\dot{V}$ max) as a function of the positive air pressure (Pn) and determining the critical air pressure (Pcrit) from the straight line at the value $\dot{V}$ max=0,
   (e) assessing on the basis of the measurement results of steps c) and d) whether the patient is experiencing a case of normal breathing (A), obstructive respiratory disturbance (B), non-obstructive respiratory disturbance (C) or snoring (D), and
   (f) maintaining or modifying the normal positive airway pressure (Pn) in accordance with the assessments of said step e).

9. The method according to claim 8 wherein the positive air pressure (1B, 1C, 1D) is decreased at intervals of time after returning each time to a preset desired value (1A) of the positive air pressure (P).

10. The method according to claim 8, wherein it is assessed that
    (a) it is a case of normal breathing (A) if a maximum respiratory gas flow ($\dot{V}$max) is measured being larger than or equal to a threshold value for respiratory gas flow ($\dot{V}$) and any values of an obstructive respiratory disturbance (B) are not assessed,
    (b) it is a case of obstructive respiratory disturbance (B) if a maximum respiratory gas flow ($\dot{V}$max) is measured as being smaller than the threshold value for respiratory gas flow ($\dot{V}$) and an obstructive respiratory disturbance (B) is assessed,
    (c) it is a case of non-obstructive disturbance (C) if a maximum respiratory gas flow ($\dot{V}$max) is measured as being smaller than the threshold value for respiratory gas flow ($\dot{V}$) and any values of an obstructive respiratory disturbance (B) are not assessed, and (d) it is a case of snoring (D) if a maximum respiratory gas flow ($\dot{V}max$) is measured as being larger than or equal to the threshold value for respiratory gas flow ($\dot{V}$) and the values of an obstructive respiratory disturbance are assessed.

11. The method according to claim 10 wherein,
(a) the preset, normal positive air pressure (Pn) is maintained if it is a case of normal breathing (A),
(b) the positive air pressure is increased if it is a case of obstructive respiratory disturbance (B),
(c) a different therapy mode is switched to if it is a case of non-obstructive respiratory disturbance (C), and
(d) the positive air pressure is increased if it is a case of snoring (D), wherein the pressure increase is terminated if, upon increase of the positive air pressure, the maximum respiratory gas flow ($\dot{V}$ max) is not further increased.

12. The method according to claim 11, wherein in case (c) the switch is from monolevel to bilevel CPAP therapy.

13. The method according to claim 10, wherein the threshold value of the respiratory gas flow ($\dot{V}$) is adjusted in accordance with physiological values of a patient.

14. The method according to claim 13, wherein the respiratory gas flow ($\dot{V}$) is measured in intervals of time which are individually adjusted to a patient.

15. The method according to claim 14, wherein the adjustment of the threshold value of the respiratory gas flow ($\dot{V}$) in accordance with physiological values of the patient is 300 ml/s.

* * * * *